(12) United States Patent
Margolin et al.

(10) Patent No.: US 9,320,596 B2
(45) Date of Patent: Apr. 26, 2016

(54) DILATOR FOR INSERTING A VOICE PROSTHESIS

(71) Applicant: Atos Medical AB, Hörby (SE)

(72) Inventors: Gregori Margolin, Stockholm (SE); Jonas Karling, Nacka (SE); Ronny Magnusson, Horby (SE)

(73) Assignee: Atos Medical AB (SE)

( * ) Notice: Subject to any disclaimer, the term of this patent is extended or adjusted under 35 U.S.C. 154(b) by 0 days.

(21) Appl. No.: 14/258,936

(22) Filed: Apr. 22, 2014

(65) Prior Publication Data

US 2014/0228952 A1    Aug. 14, 2014

Related U.S. Application Data

(62) Division of application No. 13/378,590, filed as application No. PCT/EP2010/058427 on Jun. 16, 2010, now Pat. No. 8,721,720.

(30) Foreign Application Priority Data

Jun. 16, 2009   (SE) ...................... 0950462

(51) Int. Cl.
*A61F 2/20*  (2006.01)
*A61F 2/08*  (2006.01)
*A61F 11/00*  (2006.01)
*A61B 17/24*  (2006.01)
*A61M 29/00*  (2006.01)
*A61B 17/34*  (2006.01)

(52) U.S. Cl.
CPC . *A61F 2/20* (2013.01); *A61B 17/24* (2013.01); *A61F 2/203* (2013.01); *A61M 29/00* (2013.01); *A61B 17/3468* (2013.01)

(58) Field of Classification Search
CPC .............. A61F 2/20; A61F 2/08; A61F 11/00
USPC ........................ 623/9–11.11, 14.11; 606/108; 600/114–115; 128/207.14–207.18, 192
See application file for complete search history.

(56) References Cited

U.S. PATENT DOCUMENTS 6,159,243 A     12/2000  Schouwenburg
2009/0036983 A1  2/2009  Tran

FOREIGN PATENT DOCUMENTS

DE       202008000670 U1    4/2008
(Continued)

OTHER PUBLICATIONS

European Office Action for App. No. 10722147.5 dated Dec. 18, 2014.

*Primary Examiner* — Yashita Sharma
(74) *Attorney, Agent, or Firm* — Fishman Stewart PLLC

(57) ABSTRACT

A dilator may include a substantially conical body having a tip portion at a proximal end and a base portion at a distal end thereof. A wire lock portion may be configured to lock a guide wire to the dilator. A voice prosthesis holding portion may be connected to the substantially conical body by a connecting portion. The holding portion may have a central passage configured to have a tubular body of a voice prosthesis positioned therethrough, wherein at least one flange of the prosthesis is substantially unfolded proximally of the central passage.

6 Claims, 5 Drawing Sheets

(56) References Cited

FOREIGN PATENT DOCUMENTS

| WO | WO-9635399 A1 | 11/1996 |
| WO | WO-97/23341 A1 | 7/1997 |
| WO | WO-97/41807 A1 | 11/1997 |
| WO | WO-9741807 A1 | 11/1997 |
| WO | WO-2005/097001 | 10/2005 |
| WO | WO-2005/097001 A1 | 10/2005 |

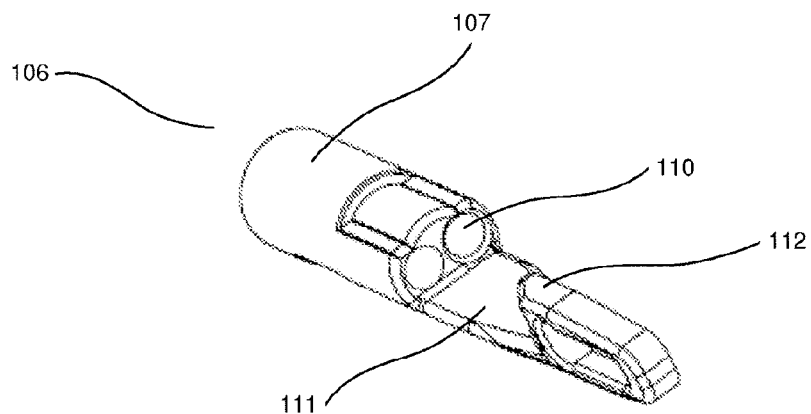
Fig. 4
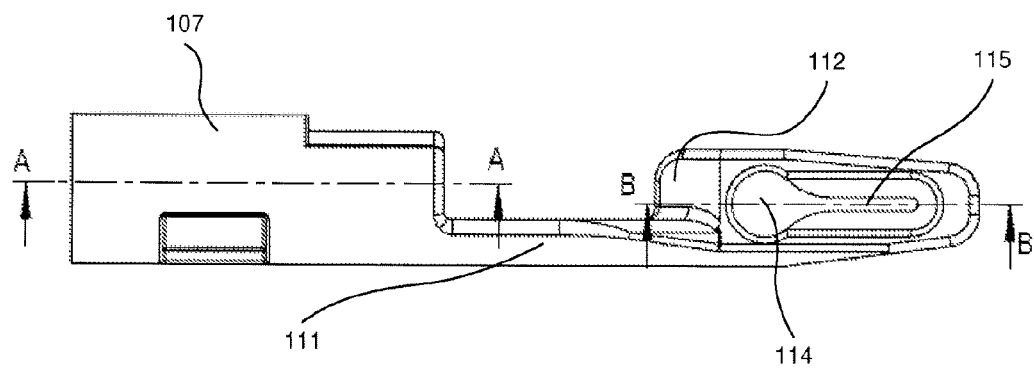
Fig. 5
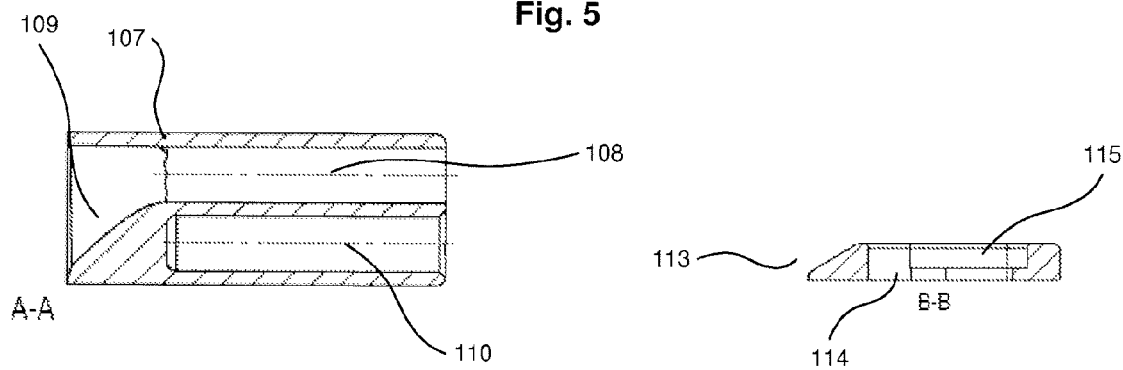
Fig. 6a
Fig. 6b

DILATOR FOR INSERTING A VOICE PROSTHESIS

CROSS-REFERENCES TO RELATED APPLICATION

This application is a divisional application of U.S. patent application Ser. No. 13/378,590, filed on Dec. 15, 2011, which claims priority to Sweden Patent Application 0950462-2 filed on Jun. 16, 2009 and PCT/EP2010/058427 filed on Jun. 16, 2010, which are hereby incorporated by reference in their entireties.

TECHNICAL FIELD

This invention pertains in general to the field of a inserting system for placement a voice prosthesis in the tracheoesophageal wall, said inserting system comprising a dilator, said dilator comprising a substantially conical body having a tip portion at the proximal end and a base portion at the distal end thereof, said dilator comprising a wire lock portion, for locking a guide wire thereto. More particularly the invention relates to a wirelock comprised in said inserting system.

BACKGROUND

In the field of laryngectomy a voice prosthesis is often used for tracheoesophagal speech. The voice prosthesis is then placed in a puncture in the tracheoesophageal wall. The voice prosthesis may be placed in said puncture directly after the voice box is removed and the trachea is sutured to the skin of the neck—so called primary puncture—or after time of surgery, under general anesthesia—so called secondary puncture. A voice prosthesis has a tubular body, with a flange in each end. The tubular body is to be mounted in the tracheoesophageal wall with a flange situated on the tracheal side, substantially hindering movement of the voice prosthesis into the oesophagus, and the other flange situated on the oesophagal side, hindering movement of the voice prosthesis into the trachea. A valve member is located in the lumen of the tubular body. The voice prosthesis may also be provided with a safety strap, arranged on the flange intended to be situated on the tracheal side.

Laryngectomy is in most cases performed in cases of laryngeal cancer.

To create a tracheoesophageal puncture during primary puncture, a pharynx protector is inserted in the esophagus until the tip of the pharynx protector reaches the intended puncture site. The pharynx protector is a hollow, rigid, and cylindrical device with a handle. It is inserted in the pharynx/esophagus to protect the posterior wall during puncture. The tip of the device has normally an oblique opening, which is palpated by the surgeon to verify the correct position for puncture. The tip of the pharynx protector is palpated through the tracheoesophageal wall to verify the correct placement of the puncture. The puncture is made with a troachar through the tracheoesophageal wall against the pharynx protector. The troachar is a thick and hollow instrument, normally made of stainless steel. The troachar is used to create the puncture and to facilitate the subsequent introduction of a guide wire, which is inserted through the hollow part of the troachar.

The guide wire may be a flexible plastic tube, which is plastically deformable. The troachar may have a bent tip in order to direct the guide wire into the hollow cylindrical part of the pharynx protector. The troachar is oriented so that a bent tip thereof directs a guide wire—subsequently inserted through the troachar—into the lumen of the pharynx protector. Next, the guide wire is introduced through the troachar until the distal tip of the guide wire extends approximately 20 cm through the pharynx protector. The troachar and the pharynx protector are removed, leaving the guide wire in place through the puncture of the tracheoesophageal wall. Thereafter, a voice prosthesis is arranged on the guidewire and pulled through the tracheoesophageal puncture.

During secondary puncture a rigid esophagoscope is generally inserted in the esophagus instead of a pharynx protector until the tip of the esophagoscope can be palpated at the puncture site. The puncture is then made with the troachar against the esophagoscope which acts as a pharynx protector.

U.S. Pat. No. 6,159,243 discloses a voice prosthesis implantation kit including; a leader element, which can be introduced via the mouth to the location where the voice prosthesis is to be implanted; a hollow cutting element for cutting the wall of oesophagus, said leader element having a first coupling device in one end; a guide element, which in one end may be coupled to said first coupling element, and in the other end carrying an dilator for a voice prosthesis. The dilator may be screwed into engagement with the guide element, said guide element having a cavity in the other end thereof, in which cavity the voice prosthesis may be mounted by pushing a flange of the voice prosthesis into the cavity. The kit according to U.S. Pat. No. 6,159,243 is only usable for secondary puncture; the voice prosthesis can not be pre-loaded in the dilator, since one of the flanges is pushed into the cavity of the voice prosthesis, whereby the risk of plastic deformation is high; the guide element is screwed into engagement with the dilator in the thin end of the dilator, putting high demands on attachment mechanism, since the pulling of the kit through the puncture wants to depart the dilator from the guide element. Also, since the kit according to U.S. Pat. No. 6,159,243 is adapted to pull the voice prosthesis through the neck into position, it is impossible to control if the inner flange is fully unfolded on the oesophagal side. Furthermore, as the oesophagal flange is folded and pushed into a gripping cavity keeping the flange in folded position, the holding force is very limited. Thus, the risk of disengagement between the cavity and the voice prosthesis is quite high; especially, since the flange of the voice prosthesis is of a substantially flexible material.

Hence, an improved inserting system would be advantageous, and in particular a dilator allowing for use in both primary and secondary puncture; allowing for pre-loading of the voice prosthesis in the dilator prior to usage, i.e. a dilator not risking plastic deformation of flanges on the voice prosthesis; a dilator allowing for a more effective and easy to assemble attachment mechanism between the dilator and the guide wire, would be advantageous.

SUMMARY

Accordingly, the present invention preferably seeks to mitigate, alleviate or eliminate one or more of the above-identified deficiencies in the art and disadvantages singly or in any combination and solves at least the above mentioned problems by providing a inserting system with a dilator, said dilator comprising a voice prosthesis holding portion connected to said substantially conical body by a connecting portion, said holding portion having a central passage, said central passage being configured to have the tubular body of the voice prosthesis positioned therethrough, such that the flanges of the voice prosthesis are substantially unfolded proximally and distally of said central passage. A wirelock comprised in said inserting system is also provided.

Advantageous features hereof are embodied in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIGS. 4, 5, 6a, and 6b illustrate one embodiment of a wire lock according to the present invention.

DETAILED DESCRIPTION

The following description focuses on an embodiment of the present invention applicable to an inserting system for inserting a voice prosthesis in the tracheoesophageal wall, and the following description focuses in particular to a dilator and a wirelock comprised therein. However, it will be appreciated that the invention is not limited to this application but may be applied to many other medical fields, wherein two-flange systems are used, including for example the insertion of valves in flexible walls.

A voice prosthesis has—as described earlier—a tubular body, with a flange in each end, said flanges extending radially and outwardly. The tubular body is to be mounted in the tracheoesophageal wall with a flange situated on the tracheal side, substantially hindering movement of the voice prosthesis into the oesophagus, and the other flange situated on the oesophagal side, hindering movement of the voice prosthesis into the trachea. A valve member is located in the lumen of the tubular body. The voice prosthesis may also be provided with a safety strap, arranged on the flange intended to be situated on the tracheal side.

Figure 1A:
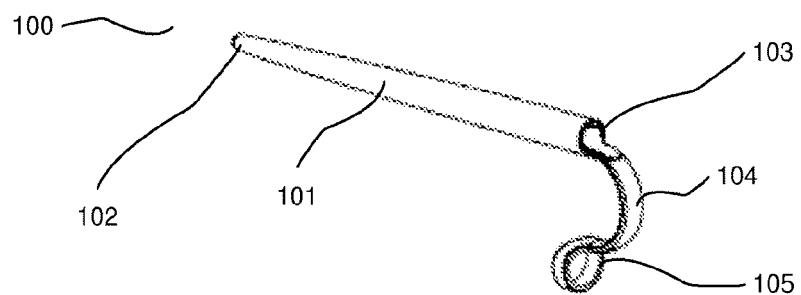
FIGS. 1a to 1c illustrate one embodiment of a dilator according to the present invention.
Figures 1B, 1C:
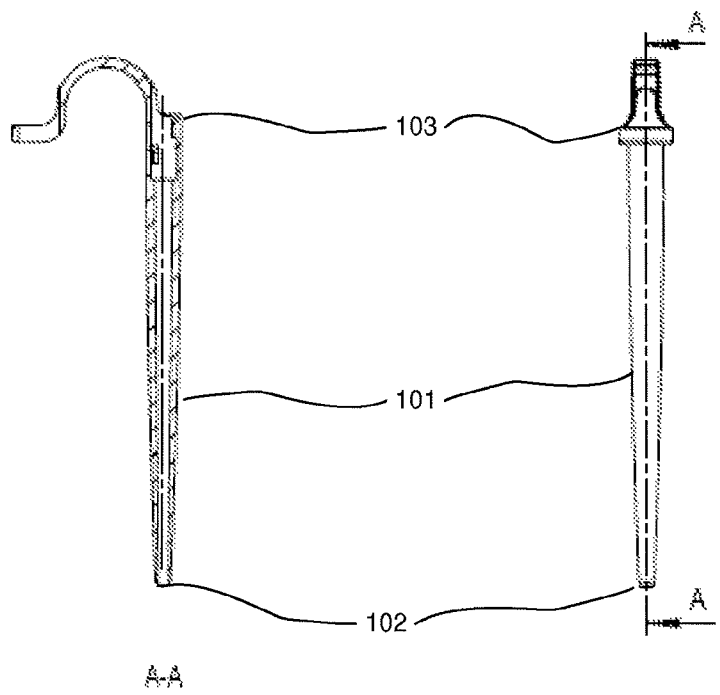

According to a first embodiment of the present invention a dilator 100 according to FIGS. 1a to 1c is provided. The dilator 100 comprises a substantially conical body 101, having a first proximal end in the tip portion 102 and a second distal end in base portion 103 of the conical body. The dilator 100 is made of a flexible material in order to adapt to the surrounding tissues during insertion. A suitable material is thermoplastic elastomers, such as styrenic block copolymers, polyolefin blends, elastomeric alloys, and thermoplastic polyurethanes. The dilator 100 is provided with a through hole or lumen from the first to the second end thereof, adapted for receiving a guide wire therethrough. The dilator 100 dilates a puncture site when the dilator 100 is being pulled through the puncture by the guide wire. In the second end the dilator is provided with a connecting portion, such as a strap 104, extending distally from said base portion 103. The strap 104 has a voice prosthesis holding portion, such as a ring 105. The holding portion thus has a central passage, said central passage being configured to have the tubular body of the voice prosthesis positioned therethrough, such that the flanges of the voice prosthesis are substantially unfolded proximally and distally of said central passage. The ring 105 is positioned in the distal end of the strap 104. Thus, the strap 104 connects the conical body 101 and the ring 105. The ring 105 is adapted in size for housing a voice prosthesis therein, such that the tubular body of the voice prosthesis is circumferenced by the ring 105, while the flanges of the voice prosthesis keep the ring 105 positioned around said tubular body. Thus, the flanges—when the voice prosthesis is in an arranged position in the holding portion of the dilator—have a greater radial extension than the inner diameter of the central passage of the holding portion. Simultaneously, the configuration of the strap 104 and the ring 105 allows for a voice prosthesis to be pre-mounted in the ring 105, without deformation of one or both of the flanges of the voice prosthesis. Thus, the dilator 100 with a preloaded voice prosthesis may be stored in ready-to-use assembly, without the need of arranging the voice prosthesis in the dilator just prior to insertion of the voice prosthesis in the tracheoesophageal wall. Also, the ring 105, attached to the strap 104, facilitates the mounting of a voice prosthesis therein, since the flanges of the voice prosthesis are workable from both sides of the ring 105, increasing the number of directions that the voice prosthesis and the ring 105 may be workably arranged from. Furthermore, the ring 105, attached to the strap 104, allows for an improved insertion of a voice prosthesis, since the ring 105 will force the proximal flange of the voice prosthesis through the tracheoesophageal wall one part at a time, due to the tilted pulling through action. Hence, only a part of the flange at a time has to be pulled through the tracheoesophageal wall, minimizing the stress on the tracheoesophageal wall.

Figure 2:
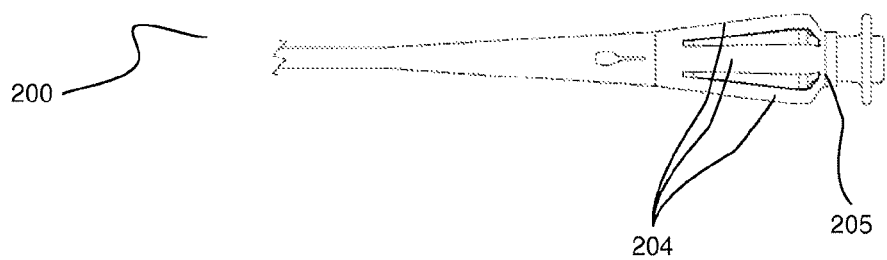
FIG. 2 illustrates another embodiment of a dilator of the present invention.

In another embodiment, according to FIG. 2, the voice prosthesis holding portion, such as dilator ring 205, is connected to the dilator 200 by the connecting portion in form of a number of flexible ribs 204. In the embodiment according to FIG. 2, a voice prosthesis is placed in the voice prosthesis holding portion. Thus, the strap 104 according to the embodiment of FIG. 1 is replaced by the flexible ribs 204 in this embodiment. The tubular body of the voice prosthesis may then be arranged in the ring 205, with one flange thereof located distally of the ring 205, while the other flange being arranged proximally of the ring 205, radially inside the flexible ribs 204. The flexible ribs 204 have a flexibility that allows the flange arranged radially inside the flexible ribs 204 to be fully unfolded. A suitable material of said ribs 204, for providing said flexability, may for example be selected from the group comprising thermoplastic elastomers, such as styrenic block copolymers, polyolefin blends, elastomeric alloys, and thermoplastic polyurethanes. Thus, the flexible ribs 204 may be formed integrally with the dilator 200. This may also be accomplished if the ribs 204, in a relaxed state, distally extends from the conical body 201 to an increased inner diameter, corresponding to the diameter of the flange of the voice prosthesis, where after the ribs 204 extends distally from said increased inner diameter to the ring 205. In this respect the flexible ribs 204 are radially bent outwards to allow the tracheal flange of the voice prosthesis to be fully unfolded. During placement the pressure of the puncture site acts on the ribs 204, which in turn fold the tracheal flange of the prosthesis forward as it passes the puncture site. The diameter of the ring 205 allows the prosthesis to be released from the ring 205 when flange on the oesophageal side reaches the esophageal wall.

Figure 3:
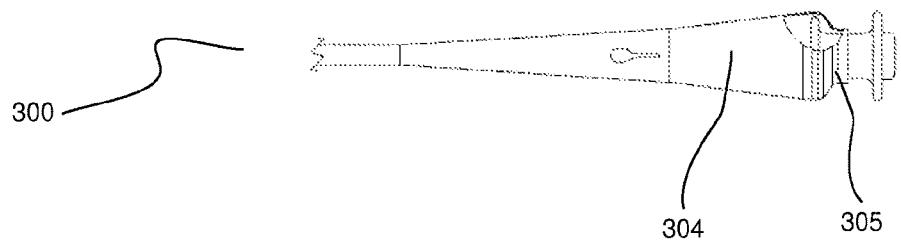
FIG. 3 illustrates another embodiment of a dilator of the present invention.

In another embodiment, according to FIG. 3, the ring 305 is connected to the conical body 301 of the dilator 300 by a connecting portion in form of a bellow shaped flexible means 304, completely surrounding the tracheal flange of the prosthesis in an unfolded state. A part of the bellow shaped flexible means 304 may be uncovered, to visualize a voice prosthesis positioned therein. The tubular body of the voice prosthesis may then be arranged in the ring 305, with one flange thereof located distally of the ring 305, while the other flange being arranged proximally of the ring 305, radially inside the flexible means 304. The flexible means 304 may have a flexibility that allows the flange arranged radially inside the flexible means 304 to be fully unfolded. This may also be accomplished if the flexible means 304, in a relaxed state, distally extends from the conical body 301 to an increased inner diameter, corresponding to the diameter of the flange of the voice prosthesis, where after the flexible means 304 extends distally from said increased inner diameter to the ring 305. In this respect the flexible means 304 is radially enlarged outwards to allow the tracheal flange of the voice prosthesis to be substantially unfolded. During placement the pressure of the puncture site acts on the substantially conical and flexible means 304, which in turn collapses and folds the tracheal flange of the prosthesis forward as it passes the puncture site. The diameter of the ring 305 allows the prosthesis to be released from the ring 305 when the esophageal flange reaches the esophageal wall.

The conical body 101—now again referring to the embodiment illustrated in FIG. 1 even though the embodiments according to FIGS. 2 and 3 are equally possible in respect of the description below—has a recess in the base portion 103, for receiving a wirelock portion 106 therein, in accordance with FIGS. 4, 5, 6a, and 6b. The wirelock portion 106 may be pre-mounted in the thick, distal end of the conical body 101 of the dilator 100. The wirelock portion 106 may for example be of a somewhat rigid plastics, such as polyvinylidene fluoride (PVDF), polypropylene (PP), and polyamide. The wirelock 106 is intended for locking the guide wire to the dilator 100. The recess is thus a part of the through hole, extending from the tip portion 102 to the base portion 103. The wirelock portion 106 has a tubular body 107, with a first proximal end and a second distal end. The wirelock portion 106 is to be inserted in the recess of the conical body with a proximal end first, such that the distal end of the cylindrical body of the wirelock portion 106 will be positioned substantially level with the base portion 103 of the conical body 101.

The wirelock portion 106 may be held in place by a radial factional grip, due to material characteristics of the conical body 101 and the wirelock portion 106. The wirelock portion 106 may also be provided with cavities on the tubular body 107, while the recess in the distal end of the conical body 101 is provided with bosses that fits into the cavities in the wirelock, to obtain maintaining effect of the wirelock portion 106 in the conical body 101. The wirelock portion 106 may also be integrated with the conical body 101.

The tubular body 107 is provided with a through hole 108 from the proximal end to the distal end thereof, and vice versa, i.e. the lumen of the tubular body 107. In the proximal end of the tubular body 107, the wire lock portion has a conically shaped recess 109, narrowing the through hole into a diameter substantially the same as a guide wire. In the distal end of the tubular body 107 a cavity 110, such as a blind hole, is provided. The cavity 110 is adapted for receiving a tip of a guide wire therein. In this respect, the diameter of the cavity 110 may be approximately the same as the diameter of a guide wire. The cavity may be located such that the extension thereof is parallel with the through hole, i.e. the lumen, through the tubular body 107. In the distal end of the tubular body 107, the wirelock portion 106 is provided with a rib 111, extending distally from the distal end of the tubular body 107. The rib 111 may extend distally from the peripheral part of the tubular body 107. Furthermore, the rib 111 may be integrated with the tubular body 107, and being of a relatively rigid plastic material. The rib 111 is provided with a tab 112, extending inwards towards a central axis of the tubular body 107. Thus, the rib 111 and the tab 112 forms a hook like element, extending distally from the distal end of the tubular body 107, and then bending towards the central axis of the tubular body 107.

In the embodiment according to FIG. 3, the connecting portion in form of the bellow shaped flexible means 304, may be provided with a slit, allowing for the guide wire to exit the flexible means 304, to be re-directed by the user back into the flexible means 304 into the cavity 110. It is also possible to provide the proximal end of the substantially conical body 101, 201, 301 with a deformable tubular element. Such deformable tubular element may be positioned in the proximal end of the substantially conical body 101, 201, 301. The guide wire may then be inserted into the lumen of the deformable tubular element, whereafter said element is deformed, for example by compression with a pair of pliers, to clamp the guide wire therein.

The tab 112 may extend towards the central axis of the cylindrical body to such an extent that it will intersect with the a plane extending in the longitudinal direction of the tubular body 107, said plane including the central axes of the recess/through hole and the cavity 110. Thus the tab 112 may block distal movement of a guide wire running through the through hole, with a tip of the guide wire being inserted in the cavity 110.

In the case the tab 112 covers distal extension in the longitudinal direction for the through hole/recess, i.e. if the tab 112 intersects with the central axis of the lumen of the tubular body 107, the surface of the tab 112 facing the tubular body 107 may be provided with a chamfer 113, said chamfer extending over the intersection of the tab 112 and the central axis of the through hole/lumen/recess, to facilitate the correct mounting of the guide wire in the wirelock portion 106. The chamfer will guide the guide wire to the side, i.e. towards the periphery of the tubular body 107.

The rib 111 may also comprise a key hole 114 in the distal end thereof, such as at the tab 112. The key hole 114 may be adapted for receiving a safety strap of a voice prosthesis carrying such safety strap. The safety strap of the voice prosthesis may then be preloaded in the wide part of the key hole 114 to avoid permanent deformation of the voice prosthesis during the product shelf life. If the voice prosthesis is prematurely dropped from the dilator ring, the prosthesis safety strap will be pulled into the narrow slit 115 of the key hole 114 and locked to the dilator 100, 200, 300. Thus, such voice prosthesis may be secured to the dilator 100 during the procedure of inserting the voice prosthesis in the wall between the trachea and oesophagus. The safety strap may also be pre-mounted into the slit 115 before the insertion of the voice prosthesis.

Figure 7A:
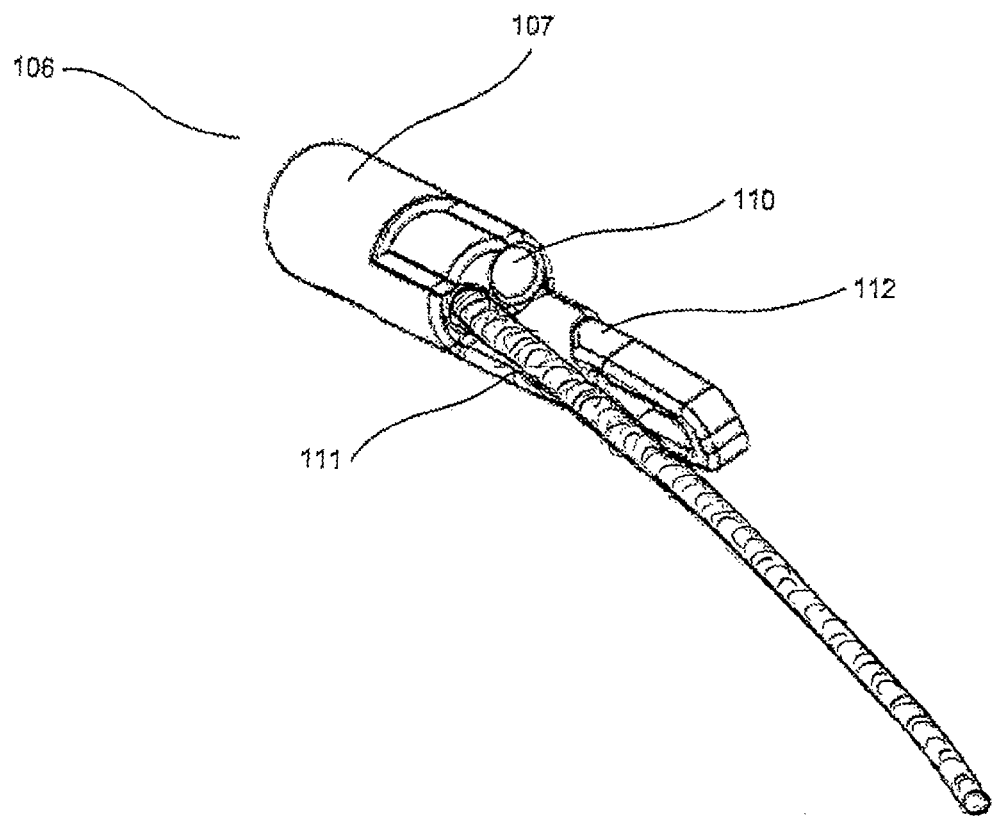
FIGS. 7a to 7c illustrates the cooperation between a guide wire and a wire lock according to an embodiment of a procedure of the present invention.
Figure 7B:
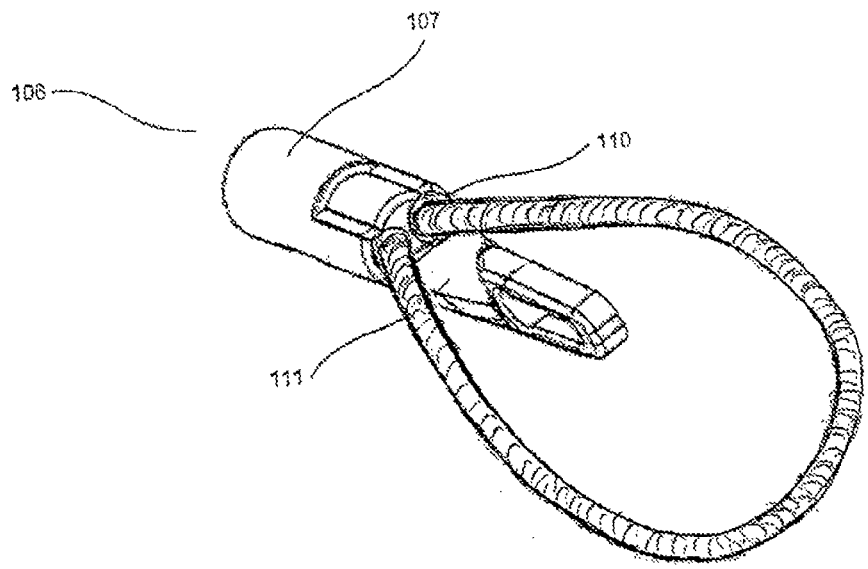

During the procedure of inserting a voice prosthesis into the tracheoesophageal wall, the guide wire is inserted through the thin, proximal end of the dilator 100. The guide wire may for example be of a suitable polymer, such as polypropylene or polyamide. The guide wire is then pushed further until it exits through the wirelock portion 106. The chamfer of the tab 112 may then guide the guide wire to the side, to facilitate the correct mounting of the guide wire in the wirelock portion 106. The guide wire may then be pulled approximately 100 to 150 mm through the wirelock portion 106 to facilitate the locking procedure, in accordance with FIG. 7a. The distal end of the guide wire is bent 180 degrees and inserted in the cavity 110 next to the through hole where the guide wire exits, in accordance with FIG. 7b. The guide wire may then be pulled in the proximal direction by pulling the part of the guide wire extending from the proximal end of the dilator 100, creating a sharp bend between the holes in the wirelock portion 106, that locks the guide wire to the wirelock portion 107, and thus also to the dilator 100, in accordance with FIG. 7c. Hence, a dilator allowing for a more effective and easy to assemble attachment mechanism between the dilator and the guide wire, is obtained, since the pulling force for pulling the dilator 100 through the puncture will only tighten the cooperation between the dilator 100 and the guide wire, without the need of threaded parts and complicated screwing motions during assembly. Other ways of fixating the guide wire to the dilator 100 is also possible, without departing from the gist of the present invention.

Figure 7C:
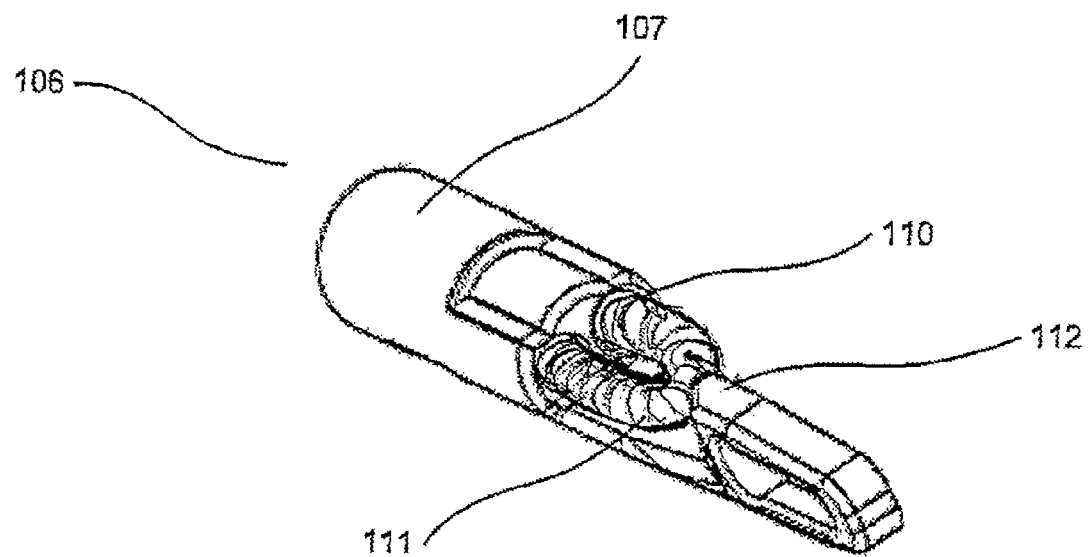

The tab 112 facing the two holes—i.e. the through hole/recess and the cavity—of the wirelock portion 106, acts as a stop preventing the guidewire from being pushed out of the cavity 110, which is also disclosed in FIG. 7c. In this respect the depth of the cavity 110 may be equal to or greater than the distance from the distal end of the cylindrical body 107 to the tab 112.

The guidewire-dilator-prosthesis assembly is pulled through the puncture site, dilating the puncture to facilitate the subsequent prosthesis placement. When the dilator 100 has passed the puncture, the voice prosthesis is pulled through the puncture by the ring 105. At the passage of the puncture the tracheal flange of the voice prosthesis is partly folded forward by the ring 105 and partly folded backward by the tissue around the puncture site. When the ring 105 passes the puncture, the ring 105 is pulled over the tracheal flange of the voice prosthesis, thus forcing said tracheal flange forward and finally unfolding in the trachea. This is specifically beneficial, since then only a part of the flange at a time has to be pulled through the tracheoesophageal wall, minimizing the stress on the tracheoesophageal wall. Finally, the prosthesis safety strap may be cut and the prosthesis may be turned in the correct position.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A dilator for inserting a voice prosthesis, said voice prosthesis comprising a tubular body and radially outwardly extending flanges in the ends of said tubular body, configured to a tracheoesophageal wall, said dilator comprising a substantially conical body having a tip portion at the proximal end and a base portion at the distal end thereof, said dilator comprising a wire lock portion, for locking a guide wire thereto, characterized in that said dilator comprising a voice prosthesis holding portion connected to said substantially conical body by a connecting portion, said holding portion having a central passage, said central passage being configured to have the tubular body of the voice prosthesis positioned therethrough, such that at least one of the flanges of the voice prosthesis is substantially unfolded proximally of said central passage, wherein said voice prosthesis holding portion is a ring portion, and wherein said connecting portion is a flexible bellow-shaped hollow portion.

2. The dilator according to claim 1, wherein said connecting portion includes a number of flexible ribs and said voice prosthesis holding portion includes a ring portion.

3. The dilator according to claim 1, wherein said flexible bellow-shaped hollow portion allows for at least one of the flanges of said voice prosthesis to be substantially unfolded therein.

4. The dilator according to claim 1, wherein the dilator is made of a flexible material.

5. The dilator according to claim 1, wherein substantially conical body has a through hole from the tip portion to the base portion.

6. The dilator according to claim 1, the base portion further comprising a recess configured to receive a wirelock comprising a tubular body with a first proximal end and a second distal end, having a cavity.

* * * * *